United States Patent
Adams et al.

(10) Patent No.: US 7,625,367 B2
(45) Date of Patent: Dec. 1, 2009

(54) TELESCOPE DRIVECABLE SUPPORT TUBE

(75) Inventors: Craig L. Adams, Rogue River, OR (US); Almira Gascon, Milpitas, CA (US)

(73) Assignee: Scimed Life Systems, Inc., Maple Grove, MN (US)

(*) Notice: Subject to any disclaimer, the term of this patent is extended or adjusted under 35 U.S.C. 154(b) by 876 days.

(21) Appl. No.: 10/727,899

(22) Filed: Dec. 3, 2003

(65) Prior Publication Data

US 2005/0124857 A1    Jun. 9, 2005

(51) Int. Cl.
*A61B 17/00* (2006.01)

(52) U.S. Cl. .............................. 606/1; 600/129; 604/264

(58) Field of Classification Search ............. 606/1, 606/6, 7, 13–16, 32, 41, 46; 607/88, 89, 607/92, 122; 600/101, 121, 129, 130; 604/264
See application file for complete search history.

(56) References Cited

U.S. PATENT DOCUMENTS

| | | | |
|---|---|---|---|
| 4,798,193 A | 1/1989 | Giesy et al. | |
| 5,120,323 A | 6/1992 | Shockey et al. | |
| 5,346,489 A * | 9/1994 | Levy et al. | 606/15 |
| 5,458,585 A | 10/1995 | Salmon et al. | |
| 5,571,114 A | 11/1996 | Devanaboyina | |
| 5,632,754 A | 5/1997 | Farley et al. | |
| 5,827,313 A | 10/1998 | Ream | |
| 5,846,259 A * | 12/1998 | Berthiaume | 606/192 |
| 5,865,178 A | 2/1999 | Yock | |
| 5,902,245 A | 5/1999 | Yock | |
| 5,957,941 A | 9/1999 | Ream | |
| 6,050,949 A | 4/2000 | White et al. | |
| 6,261,246 B1 | 7/2001 | Pantages et al. | |
| 6,443,903 B1 | 9/2002 | White et al. | |
| 6,537,254 B1 | 3/2003 | Schock et al. | |
| 7,039,450 B2 * | 5/2006 | Duarte | 600/374 |
| 2002/0147414 A1 | 10/2002 | White | |
| 2003/0083541 A1 | 5/2003 | Sullivan | |

FOREIGN PATENT DOCUMENTS

WO     WO 98/12968     5/1998

* cited by examiner

*Primary Examiner*—Ahmed M Farah
(74) *Attorney, Agent, or Firm*—Darby & Darby PC (57) ABSTRACT

A telescoping catheter is adapted to provide improved support and protection for a drive cable by providing, in addition to an outer sheath and a telescoping sheath, an inner sheath surrounding the drive cable. The outer sheath has a relatively larger diameter, to allow for a flared end of the telescoping sheath to pass freely within the outer sheath. The inner sheath protects and supports the drive cable when the telescoping catheter is extended and the drive cable would otherwise only be protected and supported by the outer sheath having a diameter too large to provide the desired amount of support and protection for the drive cable.

27 Claims, 6 Drawing Sheets

TELESCOPE DRIVECABLE SUPPORT TUBE

FIELD OF THE INVENTION

The field of the invention relates to medical devices, and more particularly to telescoping catheters such as those used to conduct ultrasonic imaging.

BACKGROUND OF THE INVENTION

In the medical arts, catheters are frequently used to diagnose and treat various disorders in a patient, such as clogged or blocked blood vessels. A catheter is introduced into a blood vessel of a patient by, for example, making an incision in the patient over the blood vessel and inserting the catheter into the blood vessel of the patient. A catheter operator such as a physician then maneuvers the catheter through the blood vessels of the patient until the catheter is properly situated to diagnose or treat the disorder. Since maneuvering a catheter within a patient can sometimes be a difficult task, requiring a high degree of care and time taken to change the position of the catheter, a type of catheter known as a telescoping catheter is frequently used to perform these diagnoses and treatments.

Conventional telescoping catheters include two basic components which are designed to telescope in relationship to each other. The first component includes a drive cable with a medical device such as an ultrasonic transducer or other imaging device mounted on the distal end of the cable. The proximal end of the cable is attached to a housing at the proximal end of the catheter. This housing contains components adapted to interface the drive cable with a power source, as well as other components, such as a flush port for introducing liquid solutions into the catheter, or other components useful to aid a physician or other operator in effectively and efficiently using the catheter to diagnose and treat a patient.

A proximal portion of the drive cable is covered by a flexible proximal sheath, which is attached to the proximal end of the catheter. This proximal sheath shields the drive cable from the external environment, thereby preventing contaminants from entering the patient via the catheter. The sheath also provides support for the drive cable, to restrain the drive cable from excessive flexing, bending, or other undesirable changes in location or angle.

The second component includes a flexible distal sheath which covers the distal portion of the drive cable. The distal end of the distal sheath may be sealed shut to prevent the distal end of the drive cable from contacting the patient directly, or it may be open, to allow the distal end of the drive cable to protrude out through the distal sheath and into the patient. This distal sheath also shields the drive cable from the external environment and provides support for the drive cable, as described above.

The proximal sheath and drive cable are adapted to telescope in relationship to the distal sheath. The telescoping relationship allows the catheter operator to move the first component including the medical device proximally and distally within the catheter, without having to move the entire catheter within the patient. This allows the catheter operator to easily change the location of the medical device within the patient.

In order to prevent the interior of the catheter from being exposed to the external environment, conventional telescoping catheters are designed to stop the telescoping movement of the proximal sheath away from the distal sheath before the proximal end of the distal sheath disengages from the distal end of the proximal sheath. For example, where the proximal sheath telescopes inside the distal sheath, the proximal end of the distal sheath may have a lip or detent extending inwardly, to catch against a corresponding lip, detent or flare on the distal end of the proximal sheath, and thereby prevent the proximal and distal sheaths from disengaging from each other. Alternatively, where the distal sheath telescopes inside the proximal sheath, the distal end of the proximal sheath may have a lip or detent extending inwardly, to catch against a corresponding lip, detent or flare on the proximal end of the distal sheath.

In order to accommodate the lip, detent or flare on the end of the innermost of the two sheaths, and still allow the two sheaths to telescope in relationship to each other, the internal diameter of the outermost of the two sheaths must be large enough to allow the lip, detent or flare to travel unimpeded along the inside of the outermost of the two sheaths. Therefore, the internal diameter of the outermost of the two sheaths is substantially larger than the external diameter of the drive cable extending along the inside of both of the sheaths.

When the telescoping catheter is fully compressed, this does not pose a problem, as the innermost of the two sheaths, whose internal diameter is only slightly larger than the external diameter of the drive cable, provides the desired support for the drive cable. However, as the telescoping catheter is being extended, the innermost sheath is retracted from covering the drive cable, leaving only the outermost sheath to provide support and protection to the drive cable. Since this outermost sheath is substantially larger in internal diameter than the external diameter of the drive cable, the drive cable is substantially unsupported and unprotected within the catheter.

Therefore, there is a need for an improved telescoping catheter.

SUMMARY OF THE INVENTION

An improved telescoping catheter includes an additional sheath around the drive cable, inside the formerly innermost sheath of the catheter body, which additional sheath extends along the portion of the drive cable which would be otherwise exposed when the innermost sheath is retracted from the drive cable during extension of the telescoping catheter. The additional sheath provides the needed support and protection for the drive cable even when the telescoping catheter is extended.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the present inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

Figure 1:
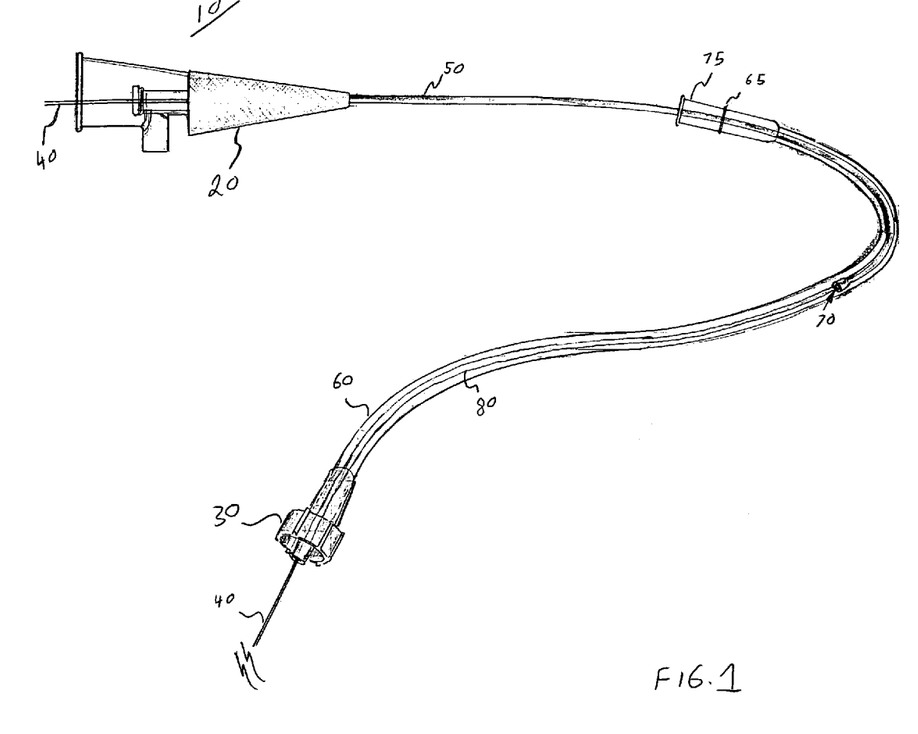
FIG. 1 depicts a catheter in accordance with an example embodiment of the invention.

An example embodiment of an improved telescoping catheter 10 is shown in FIG. 1 and described as follows. The catheter 10 includes a proximal end 20 and a member located distally from the proximal end 20, such as a hub 30. A drive cable 40 extends from the proximal end 20 of the catheter 10 along to and through the hub 30. The cable 40 extends past the hub 30, and the distal end (not shown) of the cable 40 is typically tipped with some form of medical device (not shown), such as an imaging head, an ultrasonic transducer, a light imaging device, a cutting head, or some other device. The particular device chosen for the tip of the distal end of the cable 40 is a design choice depending on the desired function for the catheter 10, and is not limited by the invention.

The cable 40 is adapted to be maneuvered within the sheaths 50, 60, 70 of the catheter 10 as desired by an operator of the catheter 10, such as an imaging technician or a physician. For example, the cable 40 may rotate an imaging device such as an ultrasound imaging device or a light imaging device, to allow images to be taken of portions of the patient's body. Additionally, the cable 40 may be extended or retracted distally or proximally to reposition the imaging device or other medical device.

The catheter 10 further includes a first sheath 50 fastened to the proximal end 20 of the catheter 10. The first sheath 50 extends distally from the proximal end of the catheter 10, surrounding a proximal portion of the cable 40. The first sheath 50 extends distally into the open proximal end of a second sheath 60, and terminates in a flared end 70. The flared end 70 is adapted to abut a corresponding detent 65 on the proximal end of the second sheath 60, to prevent the first sheath 50 from disengaging from the second sheath 60. Since the external diameter of the flared end 70 is greater than the internal diameter of the second sheath 60 as narrowed by the detent 65, the flared end 70 is prevented from passing proximally past the detent 65. In alternative embodiments, the first sheath 50 may terminate in a detent, a lip, or some other structure adapted to engage with a corresponding detent or other structure on the proximal end of the second sheath 60. Still other means of preventing the first sheath 50 from disengaging from the second sheath 60 may be used.

The second sheath 60 is attached to the proximal end of the hub 30, and extends proximally along the catheter 10, surrounding a distally located portion of the cable 40 as well as a third sheath 80, as discussed below. The second sheath 60 terminates in the proximally located detent 65. This detent 65 may be located directly on the proximal end of the second sheath 60, or it may be located on a structure attached to the proximal end of the second sheath 60, such as a receptacle 75. The detent 65 is adapted to engage the flared end 70, to prevent the second sheath 60 from disengaging from the first sheath 50, as discussed above. The internal diameter of the second sheath 60 is large enough to allow the flared end 70 of the first sheath 50 to freely move proximally and distally within the second sheath 60.

The third sheath 80 is attached to the distal end of the hub 30, and extends proximally along the catheter 10, surrounding the cable 40. The third sheath 80 extends through the hub 30, along the lumen formed by the second sheath 60, penetrating into the lumen formed by the first sheath 50, and terminating within the first sheath 50. The diameter of the lumen within the third sheath 80 is large enough to allow the cable 40 to freely move proximally and distally within the third sheath 80, yet small enough to provide improved support and protection to the rapidly rotating cable 40, and small enough (e.g. closely surrounding the cable 40) to allow the first sheath 50 to freely move proximally and distally along the third sheath 80 and within the second sheath 60. For example, if the cable 40 is 0.018 inches in diameter, the third sheath 80 may be 0.031 inches in diameter. In one representative example embodiment, polymer tubing such as polyetheretherketone (PEEK) tubing or 0.035"×0.031" MicroLumen™ Polyimide tubing is used to form the third sheath 80.

Figure 2A:
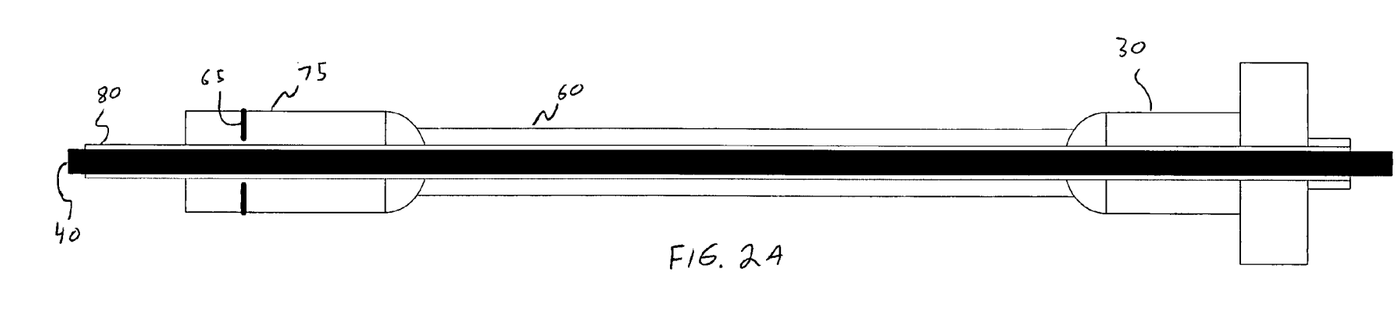
FIG. 2A depicts a side view of the distal telescoping component of the catheter of an example embodiment of the invention.
Figure 2B:
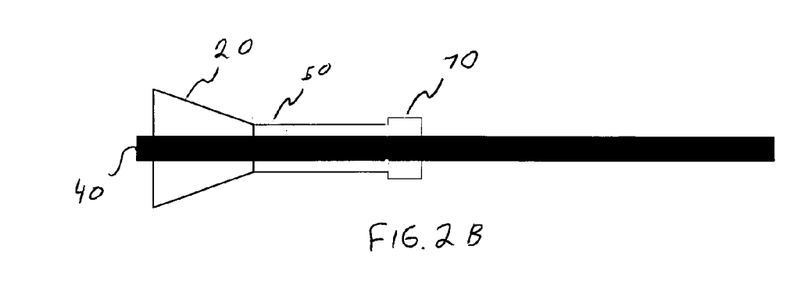
FIG. 2B depicts a side view of the proximal telescoping component of the catheter of an example embodiment of the invention.

Turning to FIGS. 2A-B, side views of the two telescoping components of the improved telescoping catheter 10 are shown. In FIG. 2A, the cable 40 extends distally through the receptacle 75, past the detent 65, and onwards through the hub 30 and out to the distal end of the catheter 10. The third sheath 80 forms a lumen for the cable 40, and extends proximally from the distal end of the hub 30 (or an attachment luer) through the hub 30, through the receptacle 75, past the detent 65 and into the open distal end of the first sheath 50, terminating within the lumen formed by the first sheath 50. The second sheath 60, including the attached receptacle 75, begins where the second sheath 60 is attached to the hub 30, and extends proximally along the cable 40 and third sheath 80, ending with the receptacle 75 attached to the proximal end of the second sheath 60. The space between the second sheath 60 and the third sheath 80, which allows the passage of the flared end 70 of the first sheath 50, can be seen in this view.

In FIG. 2B, the cable 40 extends distally from the proximal end 20 of the catheter 10, and onwards towards the distal end of the catheter 10. The first sheath 50 is attached to the proximal end 20 of the catheter 10 and extends distally along the cable 40, towards the distal end of the catheter 10. The first sheath 50 also forms a lumen for the cable 40. The increased diameter of the flared end 70 of the first sheath 50 can be seen in this view.

Figure 3:
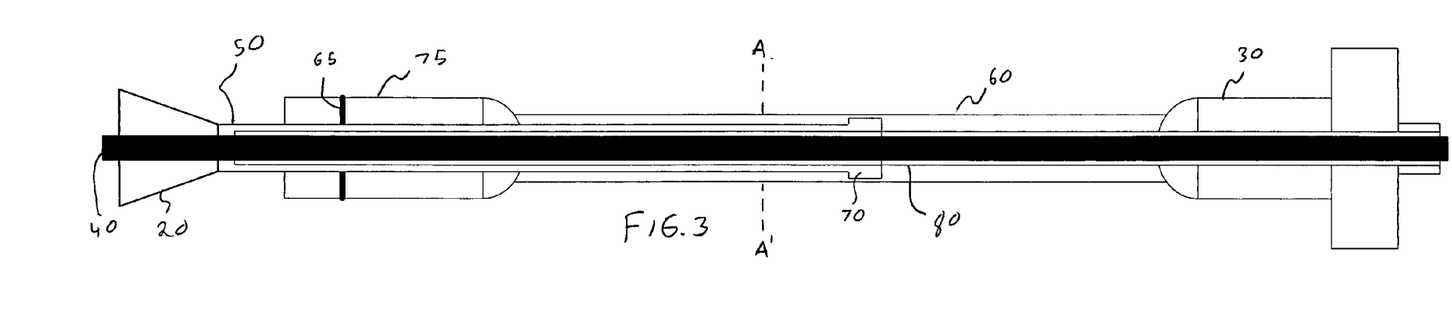
FIG. 3 depicts a side view of the catheter of an example embodiment of the invention, with the catheter partially extended.

FIG. 3 depicts a side view of the two telescoping components of the improved catheter 10, with the catheter being partially extended. The third sheath 80 extends from the hub 30 along the inside of the lumen formed by the second sheath 60 and into the lumen formed by the first sheath 50. The second sheath 60 extends from the receptacle 75 to the hub 30, surrounding the distal portion of the first sheath 50 and the proximal portion of the third sheath 80. The first sheath 50 extends from the proximal end 20 into the receptacle 75 and terminates at the flared end 70 within the lumen formed by the second sheath 60. The flared end 70 of the first sheath 50 can pass freely along the catheter 10 between the second sheath 60 and the third sheath 80.

Figure 4:
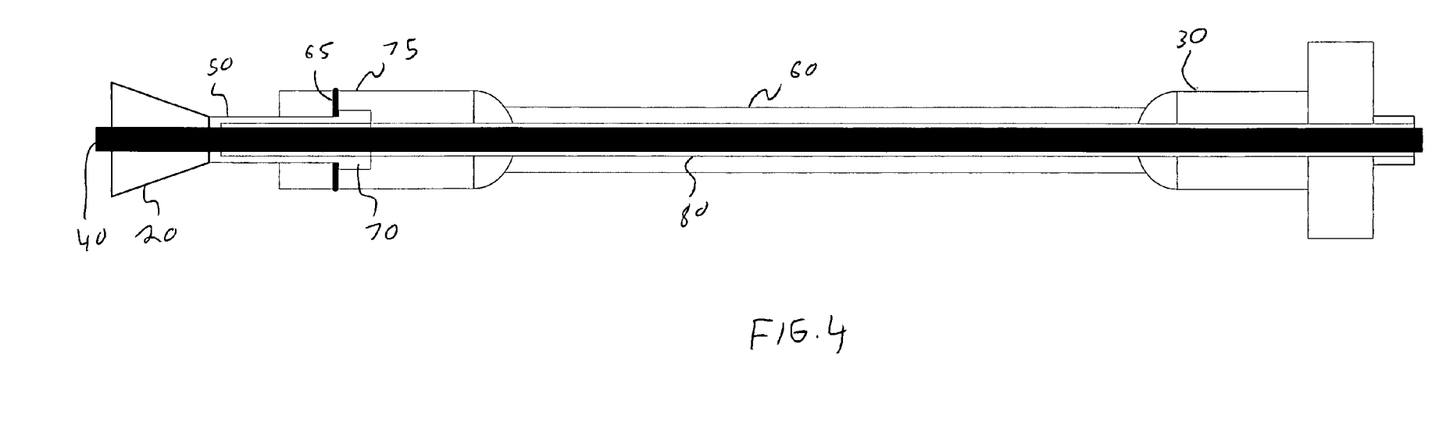
FIG. 4 depicts a side view of the catheter of an example embodiment of the invention, with the catheter extended.

FIG. 4 depicts a side view of the two telescoping components of the improved catheter 10, with the catheter 10 being fully extended. The first sheath 50 is fully retracted from within the second sheath 60, and the flared end 70, having slid proximally within the second sheath 60, abuts the detent 65 within the receptacle 75. The cable 40 is protected and supported by the third sheath 80 from any undesirable movement within the second sheath 60. Because of third sheath 80, the rapidly rotating cable 40 is not left unsupported and unprotected within the large inner lumen of second sheath 60.

Figure 5:
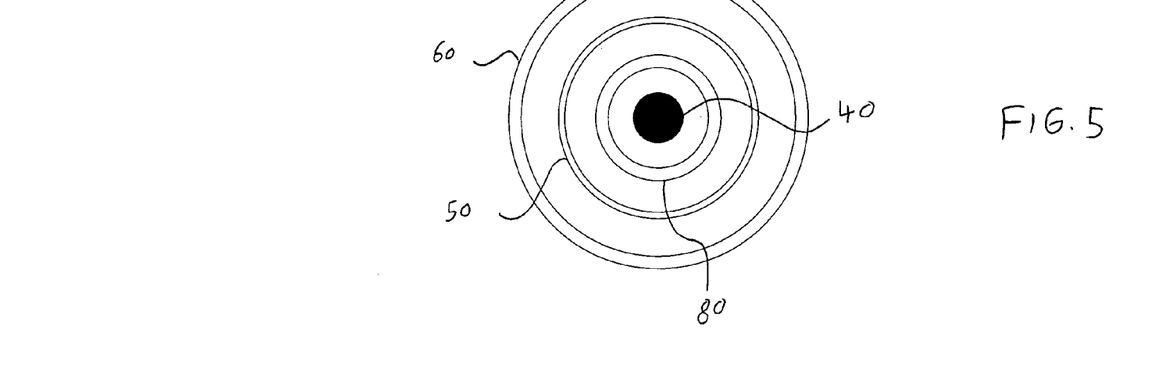
FIG. 5 depicts a cross-section of the catheter of FIG. 3.

FIG. 5 depicts a cross section of improved catheter 10 taken at the line A-A' of FIG. 3. The outermost layer of the cross-section is the second sheath 60. Within the second sheath 60 is the first sheath 50, and then the third sheath 80, and finally the cable 40. The space between the second sheath 60 and the first sheath 50 is to allow for the flared end 70 to pass along the catheter 10 when the telescoping portion of the catheter 10 is being extended or retracted.

Figure 6:
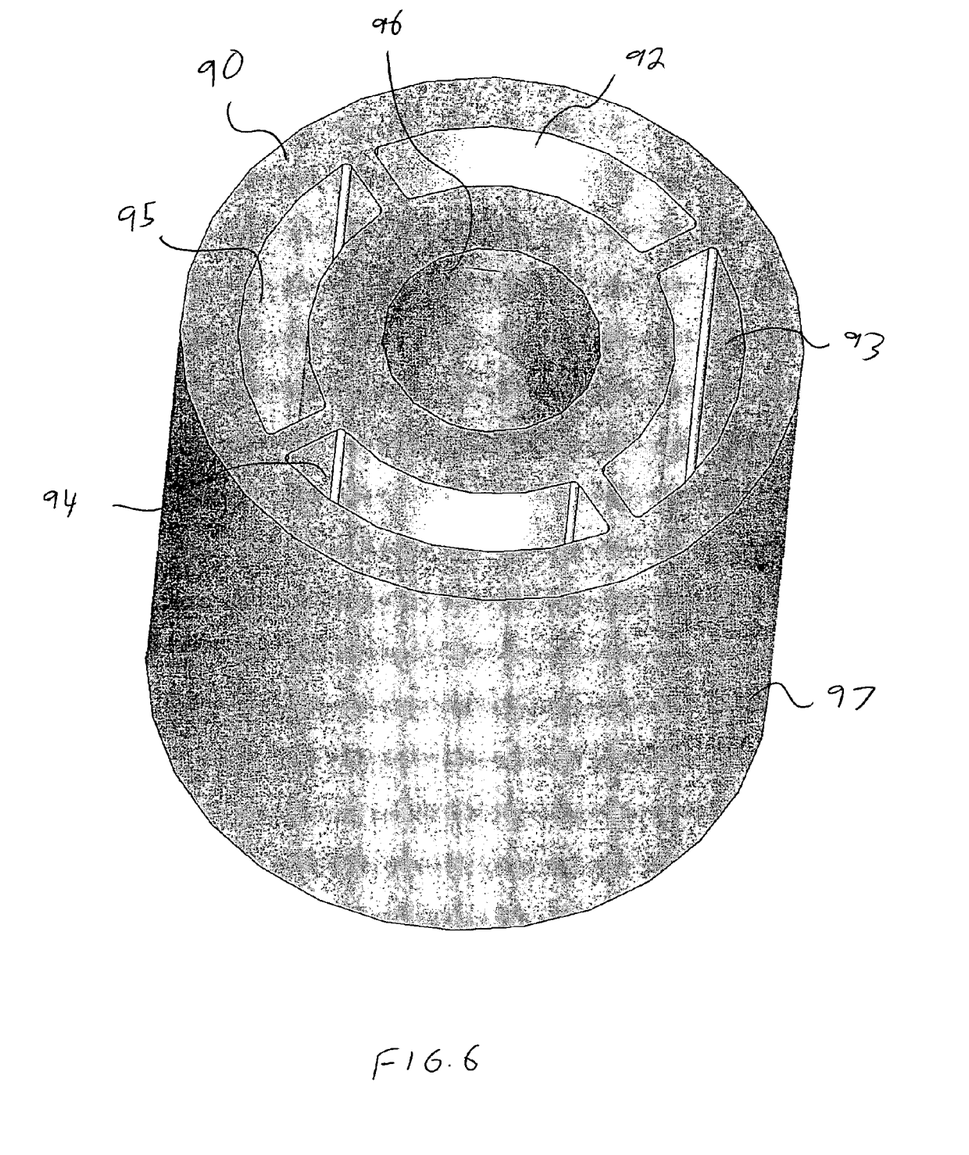
FIG. 6 depicts a spacer used in the catheter of an example embodiment of the invention.

Turning now to FIG. 6, an optional spacer 90 may be used to attach the third sheath 80 to the distal end of the hub 30. The spacer 90 includes four radially-spaced lumens 92, 93, 94, and 95, a central lumen 96, and an external surface 97. These radially-spaced lumens allow for the free flow of matter through the spacer 90 while allowing the spacer 90 to provide a convenient attachment point for the third sheath 80. Thus, the catheter 10 may be flushed with liquids while still providing support and protection for the cable 40.

The distal end of the third sheath 80 is attached to the inside of the central lumen 96, and the spacer 90 is then attached to the distal end of the hub 30 by attaching the external surface 97 of the spacer 90 to the inside of the distal end of the hub 30. These attachments may be made in a variety of ways, including, for example, a frictional engagement between the third sheath 80 and the spacer 90, or between the spacer 90 and the hub 30. Alternatively as another example, a glue or adhesive may be used to affix the third sheath 80 to the spacer 90 or the spacer 90 to the hub 30.

Figure 7:
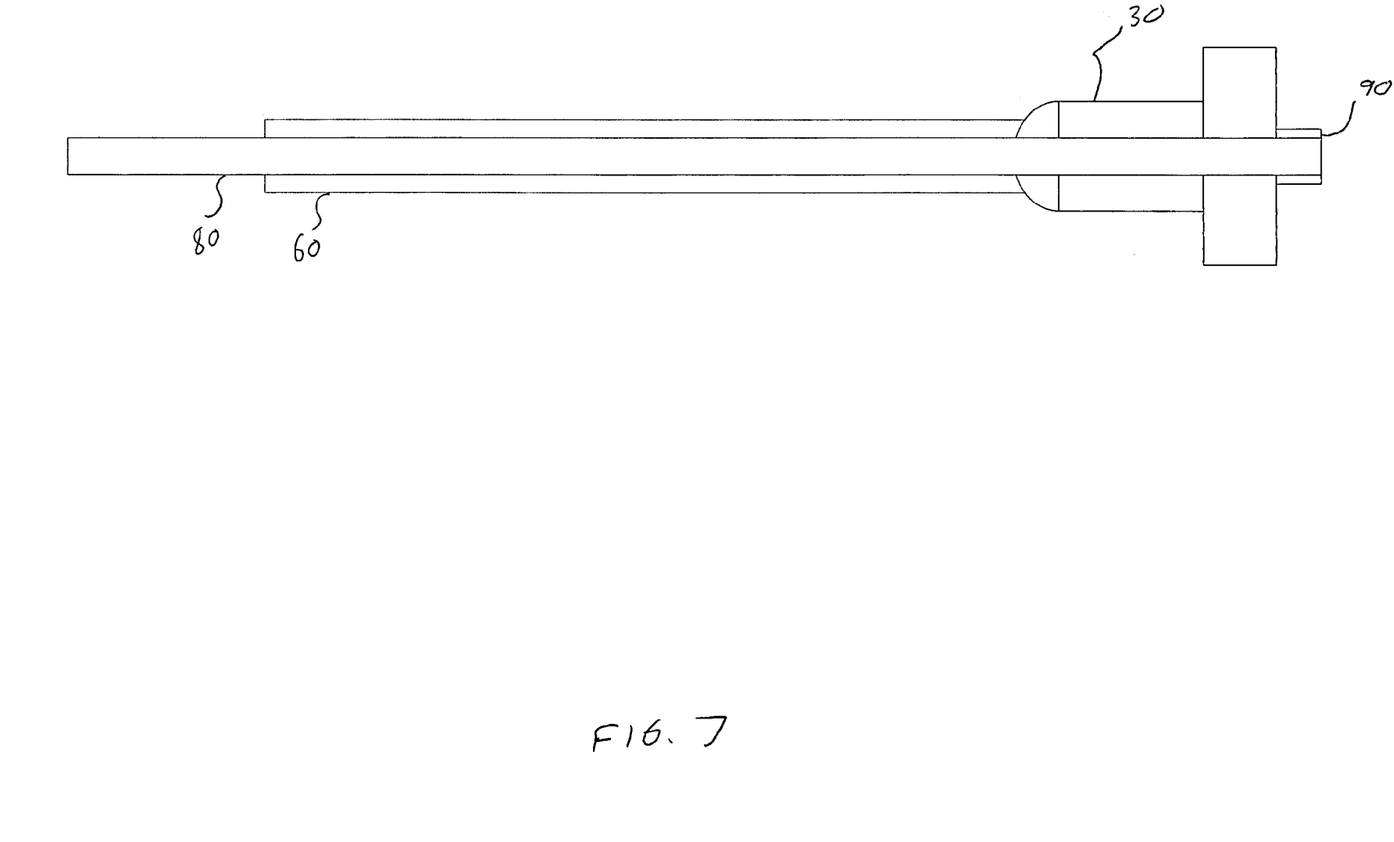
FIG. 7 depicts the distal telescoping component of the catheter of an example embodiment of the invention, including the spacer of FIG. 6.

Turning to FIG. 7, the distal telescoping component of the improved catheter 10 is shown, without the cable 40. The spacer 90 has been inserted into the distal end of the hub 30, and the distal end of the third sheath 80 has been attached to the inside of the central lumen 96 of the spacer 90, thus allowing the free flow of matter along the interior of the catheter 10, while allowing the third sheath 80 to provide support and protection for the cable 40.

In the foregoing specification, the invention has been described with reference to specific embodiments thereof. It will, however, be evident that various modifications and changes may be made thereto without departing from the broader spirit and scope of the invention. For example, the orientation of the various sheaths could be reversed, such that the first sheath is attached to the hub, and the second and third sheaths are attached to the proximal end of the catheter. The telescoping relationship would be preserved, but the outermost second sheath and innermost third sheath would be proximal to the first sheath rather than distal to the first sheath. The sheaths could have cross-sections other than circular, such as elliptical, triangular or some other shape. The cable could be replaced by some other structure in need of being supported and protected, such as a wire or fiber optic channel for delivering electricity or light, including laser light, to the distal end of the catheter. Further, other additional features such as a balloon, stent, drug delivery system, sensor for a medical positioning system, and other features known to those of skill in the art of medical devices may be included as desired. The specification and drawings are, accordingly, to be regarded in an illustrative rather than restrictive sense, and the invention is not to be restricted or limited except in accordance with the following claims and their legal equivalents.

We claim:

1. A telescoping catheter adapted for use within a human body, the catheter comprising:
   a proximal end;
   a telescoping section comprising a distal end;
   a cable extending from the proximal end to the distal end;
   a first sheath coupled to the proximal end, the first sheath extending distally along the cable and substantially surrounding the cable when the catheter is fully retracted;
   a second sheath coupled to the distal end, the second sheath extending proximally from the distal end and substantially surrounding the cable when the catheter is fully retracted, the second sheath adapted to slideably engage the first sheath so as to extend or retract the catheter; and
   a third sheath coupled to the distal end and located within the second sheath, the third sheath extending proximally along the cable through at least a portion of each of the first sheath and the second sheath when the catheter is fully extended and closely surrounding the cable from the distal end to a point within the first sheath beyond a proximal end of the second sheath.

2. The catheter of claim 1, wherein the third sheath is adapted to slide within the first sheath.

3. The catheter of claim 1, wherein the third sheath is formed of polymer.

4. The catheter of claim 3, wherein the polymer comprises polyetheretherketone.

5. The catheter of claim 3, wherein the polymer comprises polyimide.

6. The catheter of claim 1, wherein one end of the third sheath is coupled or connected to a hub at the distal end of the telescoping section.

7. The catheter of claim 1, wherein the first sheath is adapted to slide in a female relationship with the third sheath, and a male relationship with the second sheath.

8. The catheter of claim 1, wherein the proximal end comprises a flush port housing.

9. The catheter of claim 1, further comprising a spacer that couples the third sheath to the distal end.

10. The catheter of claim 9, wherein the spacer includes a plurality of radially spaced lumens.

11. The catheter of claim 9, wherein the spacer includes a central lumen.

12. A telescoping catheter comprising:
   a cable extending longitudinally along the catheter;
   a telescoping section extending longitudinally along the catheter, the telescoping section comprising a distal end;
   a flexible inner sheath coupled to the distal end and defining a first lumen for housing the cable;
   a flexible outer sheath coupled to the distal end and defining a second lumen, the outer sheath adapted to substantially surround the inner sheath; and
   a flexible telescoping sheath adapted to telescope within the second lumen and defining a third lumen adapted to substantially surround the inner sheath when the catheter is fully retracted,
   wherein the inner sheath closely surrounds the portion of the cable that lies between the distal end of the telescoping section and a proximal end of the outer sheath when the catheter is fully extended.

13. The catheter of claim 12, wherein the outer sheath is adapted to substantially surround the inner sheath within the second lumen.

14. The catheter of claim 12, wherein the inner sheath and the outer sheath are fixed in relationship to each other, and the telescoping sheath is adapted to slide in a telescoping manner between the outer sheath and the inner sheath.

15. The catheter of claim 12, further comprising a proximal end and a member located distally from the proximal end, wherein the telescoping sheath is attached to the proximal end and the inner and outer sheaths are attached to the member.

16. The catheter of claim 12, further comprising a proximal end and a member located distally from the proximal end, wherein the inner and outer sheaths are attached to the proximal end, and the telescoping sheath is attached to the member.

17. The catheter of claim 12, wherein the first lumen is adapted to receive the cable.

18. The catheter of claim 17, wherein the cable comprises a fiber optic channel.

19. The catheter of claim 17, wherein the cable comprises an electrically conductive cable.

20. The catheter of claim 12, wherein the inner sheath is formed of polymer.

21. The catheter of claim 20, wherein the polymer comprises polyetheretherketone.

22. The catheter of claim 20, wherein the polymer comprises polyimide.

23. The catheter of claim 12, further comprising a spacer that couples the inner sheath to a distal end of the catheter.

24. The catheter of claim 23, wherein the spacer includes a plurality of radially spaced lumens.

25. The catheter of claim 23, wherein the spacer includes a central lumen.

26. A telescoping catheter adapted for use within a human body, the catheter comprising:
   a cable; and
   a telescoping section extending longitudinally along the catheter and having a distal end, the telescoping section comprising
   a flexible inner sheath coupled to the distal end and defining a first lumen for housing the cable, wherein the inner sheath closely surrounds a portion of the cable;
   a flexible outer sheath coupled to the distal end and defining a second lumen, wherein the outer sheath and the inner sheath are fixed in relationship to each other, and the outer sheath substantially surrounds the inner sheath; and
   a flexible telescoping sheath, wherein the telescoping sheath is adapted to slide between the inner sheath and the outer sheath for telescoping the catheter, and defining a third lumen adapted to substantially surround the inner sheath when the catheter is fully retracted and surround a portion of the cable when the catheter is fully extended.

27. The catheter of claim 26, wherein the telescoping sheath comprises a flared end and the outer sheath comprises a detent adapted to engage the flared end of the telescoping sheath to prevent the telescoping sheath from disengaging the outer sheath.

* * * * *

UNITED STATES PATENT AND TRADEMARK OFFICE
CERTIFICATE OF CORRECTION

PATENT NO.       : 7,625,367 B2                                              Page 1 of 1
APPLICATION NO.  : 10/727899
DATED            : December 1, 2009
INVENTOR(S)      : Adams et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1544 days.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,625,367 B2 | Page 1 of 1 |
| APPLICATION NO. | : 10/727899 | |
| DATED | : December 1, 2009 | |
| INVENTOR(S) | : Craig L. Adams et al. | |

It is certified that error appears in the above-identified patent and that said Letters Patent is hereby corrected as shown below:

Title page, item [73] Assignee, delete "SciMed Life Systems, Inc." and insert -- Boston Scientific SciMed, Inc. --, therefor.

Signed and Sealed this
Twenty-eighth Day of December, 2010

David J. Kappos
*Director of the United States Patent and Trademark Office*